(12) United States Patent
Chevassus et al.

(10) Patent No.: US 10,044,996 B2
(45) Date of Patent: Aug. 7, 2018

(54) METHOD FOR PROJECTING VIRTUAL DATA AND DEVICE ENABLING THIS PROJECTION

(71) Applicant: AIRBUS GROUP SAS, Paris (FR)

(72) Inventors: Nicolas Chevassus, Chaville (FR); Denis Marraud, Issy les Moulineaux (FR); Antoine Tarault, Paris (FR); Xavier Perrotton, Chatillon (FR)

(73) Assignee: AIRBUS, Blagnac (FR)

( * ) Notice: Subject to any disclaimer, the term of this patent is extended or adjusted under 35 U.S.C. 154(b) by 0 days.

(21) Appl. No.: 14/719,307

(22) Filed: May 21, 2015

(65) Prior Publication Data

US 2015/0350617 A1 Dec. 3, 2015

(30) Foreign Application Priority Data

May 27, 2014 (FR) ..................................... 14 54761

(51) Int. Cl.
| | |
|---|---|
| *H04N 9/31* | (2006.01) |
| *G06K 9/00* | (2006.01) |
| *G09F 19/18* | (2006.01) |
| *G03B 17/54* | (2006.01) |
| *G01N 21/956* | (2006.01) |

(52) U.S. Cl.
CPC ......... *H04N 9/3185* (2013.01); *G01N 21/956* (2013.01); *G03B 17/54* (2013.01); *G06K 9/00214* (2013.01); *G09F 19/18* (2013.01); *H04N 9/3141* (2013.01); *H04N 9/3191* (2013.01); *H04N 9/3194* (2013.01)

(58) Field of Classification Search
CPC ... G01D 7/00; G01S 5/16; G06K 9/00; G06K 9/64; G06F 3/14; H04N 5/74; H04N 9/31; H04N 13/00; B25H 7/00; B64F 5/00; G01B 11/00; G01B 11/25; G02B 27/18; G03B 21/00; G03B 21/26; G06T 19/00; G09F 19/18
See application file for complete search history.

(56) References Cited

U.S. PATENT DOCUMENTS

| | | | | |
|---|---|---|---|---|
| 5,114,224 A | * | 5/1992 | Miyamoto | ............... G09F 19/18 |
| | | | | 353/122 |
| 6,860,640 B2 | * | 3/2005 | Matsuyama | .......... F16C 19/364 |
| | | | | 384/450 |

(Continued)

FOREIGN PATENT DOCUMENTS

| | | |
|---|---|---|
| EP | 1 719 580 A2 | 11/2006 |
| EP | 2 400 261 A1 | 12/2011 |

(Continued)

*Primary Examiner* — Sultan Chowdhury
*Assistant Examiner* — Danell L Owens
(74) *Attorney, Agent, or Firm* — Im IP Law; C. Andrew Im

(57) ABSTRACT

A method for projecting information issued from a digital design model. Calibration is performed by acquiring characteristic data originating from a surface of interest and comparing the characteristic data with virtual data issued from the digital design model. A spatial position of a projecting device is determined. The projecting device comprises a video projector and at least two separate image-capturing devices. Depending on the spatial position, information issued from the digital design model is projected by the video projector onto the surface of interest.

16 Claims, 2 Drawing Sheets

(56) References Cited

U.S. PATENT DOCUMENTS

| | | | |
|---|---|---|---|
| 2004/0184013 A1* | 9/2004 | Raskar | G03B 37/04 353/121 |
| 2005/0110964 A1* | 5/2005 | Bell | G06F 3/011 353/122 |
| 2006/0215120 A1* | 9/2006 | Belliveau | F21V 29/02 353/30 |
| 2008/0229254 A1* | 9/2008 | Warner | G06F 3/04812 715/856 |
| 2009/0086199 A1 | 4/2009 | Troy et al. | |
| 2009/0195753 A1 | 8/2009 | Dill et al. | |
| 2010/0225746 A1* | 9/2010 | Shpunt | G01B 11/2518 348/50 |
| 2010/0309340 A1* | 12/2010 | Border | H04N 5/335 348/241 |
| 2012/0219699 A1* | 8/2012 | Pettersson | B05B 12/122 427/8 |
| 2013/0100282 A1* | 4/2013 | Siercks | G01B 11/2513 348/135 |
| 2014/0015963 A1 | 1/2014 | Klaas | |
| 2014/0160115 A1* | 6/2014 | Keitler | G01B 11/00 345/419 |
| 2015/0350618 A1* | 12/2015 | Meier | H04N 9/3185 345/7 |

FOREIGN PATENT DOCUMENTS

| | | | | |
|---|---|---|---|---|
| JP | 04157005 A | * | 5/1992 | B21B 37/78 |
| WO | 2012/136345 A2 | | 10/2012 | |

* cited by examiner

METHOD FOR PROJECTING VIRTUAL DATA AND DEVICE ENABLING THIS PROJECTION

RELATED APPLICATIONS

This application claims priority from French Patent Application No. 14 54761 filed May 27, 2014, which is herein incorporated by reference in its entirety.

FIELD OF THE INVENTION

The present invention relates to a method for projecting, onto a surface of interest, virtual data originating from a digital design model produced by an engineering and design department.

It is applicable to many fields, especially the aeronautical, construction, shipbuilding or even aerospace fields.

The present invention is more particularly applicable to large objects such as aircraft, helicopters or even satellites, during stages of construction, assembly or even maintenance thereof.

BACKGROUND OF THE INVENTION

Knowledge of the state of an actual object during manufacture or even during operation is often partial. A manufacturer generally has at their disposal collections of measurements in folders of files (for example spreadsheets, photos or files of measurements) or in databases. It is then difficult, and in particular for large objects, not only to locate the data issued from actual measurements associated with a particular zone and to ascertain where the measurements were actually carried out, but above all to work out how they relate and correspond to each other or to a three-dimensional digital design model. Thus, ascertaining a state during manufacture or operation is not easy.

During installation, assembly and maintenance operations, an operator is required to carry out many tasks such as executing procedures, taking measurements, carrying out diagnostics, reporting on the work carried out, etc.

The operator generally uses paper plans or blueprints to ascertain and locate the various tasks to be carried out. He will also use conventional measuring means such as a measurement tape. This way of working may prove to be time-consuming, and errors may occur (positioning errors, damage, incorrect references, etc.).

One way of carrying out these tasks more rapidly and effectively is to project the information directly onto a surface of interest. The surface of interest corresponds to the surface with which the operator must interact.

It is for example possible to use a laser marking system such as that described in United States patent application US 2009/0195753 A1. This application discloses a device for the projection of laser markings onto the exterior of a vehicle, comprising a plurality of laser projectors, an image of the exterior of the vehicle projected in a synchronised form by said laser projectors, a computer connected to the laser projectors and a workstation connected to the laser projectors by way of the computer and allowing the images projected by the laser projectors to be coordinated. However, this information-projecting device is complex to implement and only allows a small amount of information to be displayed because of the inherent limitations of laser projection (Nicker, loss of brightness).

A rather similar device is described in European patent application No. EP 1 719 580 A2. Specifically, this patent application discloses a device for projecting information onto a surface of interest by way of laser projectors. This device uses metrological emitters allowing, by way of metrological receivers positioned on the surface of interest and on the laser projectors, the position and orientation of the latter to be ascertained. However, this device possesses the same limitations as the preceding system and is therefore limited in terms of the type of information that can be displayed. In addition, the system of calibration is time-consuming because of the need to position various metrological emitters and receivers.

Another known type of projection means employs a video projector and a single video camera. This system is difficult and time-consuming to implement because it requires markers to be positioned beforehand in precise positions on the surface of interest.

At the present time, every known information projecting solution is unfortunately either complex, inflexible and difficult to move, or time-consuming to calibrate. Therefore, these methods prove to be ineffective and unusable in most assembly operations. Furthermore, they are generally designed to carry out a single very specific task, such as the designation of a position or only the tracking of targets.

There is therefore, at the present time, a clear need to be able to carry out more simply and effectively, movable and flexible projection of information with a high degree of precision.

SUMMARY OF THE INVENTION

The present invention aims to alleviate all or some of the drawbacks of the prior art by providing a device allowing a method for projecting information that is precisely tailored to the environment to be implemented.

For this purpose, according to a first aspect, the present invention relates to a method for projecting information issued from a digital design model, comprising the following steps:
  a calibrating step comprising acquiring characteristic data originating from a surface of interest, comparing said characteristic data with virtual data issued from the digital design model, and determining a spatial position of a projecting device comprising a video projector and at least two separate image-capturing devices; and
  a step of projecting, depending on said spatial position, information issued from the digital design model, by means of said video projector, onto said surface of interest.

The characteristic data represent a virtual reconstruction of the three-dimensional structure of the surface of interest obtained by correlating the data acquired by each of said image-capturing devices.

By virtue of these measures, the invention allows a three-dimensional structure of a surface of interest to be analysed and makes it possible to guide an operator tasked with carrying out fitting operations or with quality control of said surface of interest. In the case of a fitting operation, the invention will for example make it possible to project the outline of a piece of equipment to be installed onto a part. In the case of a quality control operation, the invention will for example allow the three-dimensional structure of the digital design model to be projected onto the three-dimensional structure of the surface of interest, thus allowing the operator to observe any differences between the two structures. Moreover, it is easier to determine the spatial location of characteristic points of the surface of interest in said digital design model because the invention makes it possible to do away with a prior step of positioning markers in precise positions on the surface of interest with the aim of pinpointing, in a digital design model, the spatial position of information relating to the surface of interest using the spatial position of said markers. This step of positioning markers is often a source of errors as regards the precision of the positioning.

In some embodiments, the calibrating step comprises the following substeps: projecting calibration patterns onto said surface of interest; analysing said calibration patterns and creating a set of correspondences between the image-capturing devices and the video projector; and determining the spatial position of the image-capturing devices and of the video projector depending on a correspondence maximum. These embodiments allow the spatial position of the video projector relative to the image-capturing devices to be precisely determined and then the spatial position of the projecting device relative to the surface of interest to be determined.

In some embodiments, the calibrating step is carried out continuously in the following way: by projecting, in addition to the digital design model and continuously, said calibration patterns and tailoring the calibration to the surface of interest; and by analysing the patterns with the image-capturing devices and continuously determining the spatial position of said image-capturing devices and of the video projector. In particular, these embodiments allow the spatial position of the video projector relative to the image-capturing devices and of the projecting device relative to the surface of interest to be determined continuously and, more precisely, each time a new image is extracted. This for example makes it possible to alleviate problems with the precision of the calibration when the device enabling the projection is able to move and when parasitic movements occur between the image-capturing devices and the video projector.

According to some embodiments, the method comprises steps of detecting and highlighting differences between said digital design model and reality.

According to some embodiments, the method comprises steps for determining the spatial position of and tracking known movable objects in the field of view of the image-capturing devices. This makes it easier for the operator to interact with the surface of interest.

According to some embodiments, the method comprises steps allowing vibrations to be compensated for and steps allowing an alarm to be raised in the case where it is not possible to carry out this compensation. This makes it possible to prevent errors due to parasitic movements of the projector and image-capturing devices, especially via changes to the settings of said image-capturing devices.

According to some embodiments, the method comprises steps that make it possible to prevent shadowing on the surface of interest.

According to some embodiments, the method comprises steps allowing the projections to be carried out in three dimensions. This will make it easier for an operator equipped with active glasses to see the information.

According to another aspect, the present invention relates to a device for projecting information issued from a digital design model, comprising a video projector, a computer and at least two image-capturing devices and furthermore comprising means for:
  acquiring characteristic data originating from a surface of interest;
  comparing said characteristic data with virtual data issued from the digital design model;
  determining a spatial position of said image-capturing devices, of said video projector and of said projecting device; and
  for projecting, depending on said spatial position, information issued from the digital design model by means of said video projector, onto said surface of interest.

The computer allows data to be managed between the image-capturing devices, the digital design model and the video projector.

In some embodiments, the image-capturing devices are global-shutter video cameras. This has the advantage of preventing image deformation related to movement of the devices.

In some embodiments, the device for projecting virtual data comprises at least two sources of infrared light. This makes it possible for the image-capturing devices to track any collaborative object comprising infrared targets moving in the field of view of the image-capturing devices. This makes it easier for the operator to interact with the surface of interest.

In some embodiments, the device for projecting virtual data comprises a means able to adjust the settings of the image-capturing devices depending on vibrations and to emit an alarm signal when the vibrations are too great. This allows the quality of the image projected to be improved by adapting the projection settings to vibration-related constraints.

In some embodiments, the means able to adjust the settings of the image-capturing devices depending on vibrations and to emit an alarm signal when the vibrations are too great comprises an inertial sensor rigidly fastened to the video projector. This inertial sensor allows vibrations to be detected.

In some embodiments, the video projector is mounted on an instrumented mechanical system comprising a position sensor and optionally motorised. This makes it possible to reposition the video projector so as to enlarge or shrink the zone covered by the projection. In addition, the position issued from the position sensor allows the spatial position of the projecting device in the digital design model to be updated.

In some embodiments, the device for projecting virtual data comprises an autonomous power supply system. These measures have the advantage of making the device more mobile.

In some embodiments, all the elements of the device for projecting information issued from a digital design model are grouped into two housings, the first containing the video projector and the image-capturing devices and the second containing the computer and the power supply. This provides the invention with an advantage as regards transportation and the mobility of the device, which will allow the operator to handle it with ease.

In some embodiments, the two housings, in which all the elements of the projecting device are grouped, may be stacked one on the other.

BRIEF DESCRIPTION OF THE DRAWINGS

The invention will be better understood from the description, given below and merely by way of illustration, of one embodiment of the invention, this description referring to the figures, in which.

DETAILED DESCRIPTION OF EMBODIMENTS OF THE INVENTION

Figure 1:
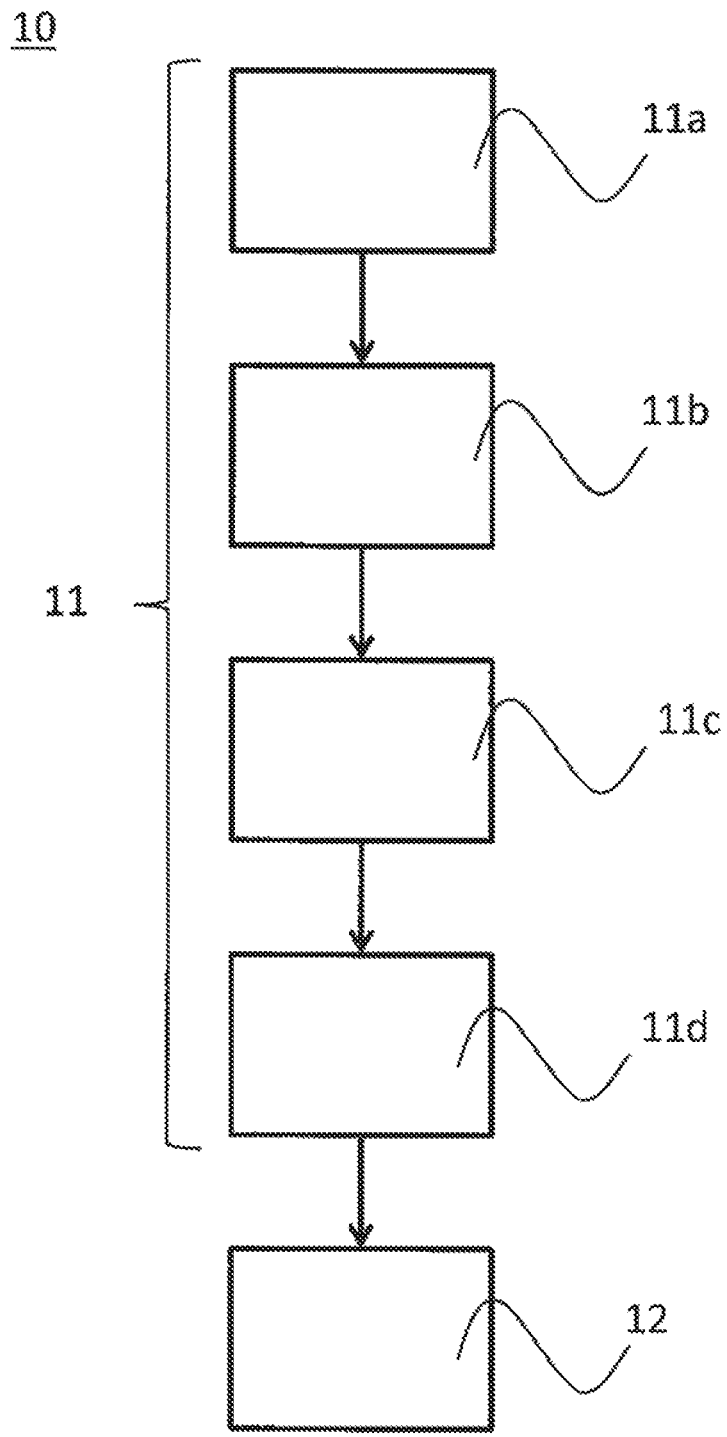
FIG. 1 is a flowchart showing the method according to one embodiment of the invention.

FIG. 1 is a flowchart showing the method 10 according to one embodiment of the invention. In a first step 11, a calibration is carried out. This step 11 comprises a substep 11a of projecting, using a video projector 19, calibration patterns onto a surface of interest 20 that may be seen in FIG. 2. In a subsequent substep 11b, at least two image-capturing devices will acquire characteristic data by analysing the calibration patterns projected onto the surface of interest 20. Specifically, the image-capturing devices 18 capture the rendering of the pattern on the surface of interest 20 and said rendering is then analysed by computer 21 in order to be expressed as a set of characteristic data forming a three-dimensional structure. In a subsequent substep 11c, the characteristic data are compared with data issued from a digital design model thus allowing, by way of a vision algorithm, a set of correspondences between the image-capturing devices 18 and the video projector 19 to be created. Lastly, in a substep 11d, the spatial position of the video projector 19 relative to the image-capturing devices 18 is determined depending on a maximum correspondence established between them by said algorithm. The spatial position of the projecting device 22, comprising the video projector 19 and the image-capturing devices 18, relative to the surface of interest, is then determined. In a last step 12, depending on the determined spatial position of the projecting device 22, information associated with virtual data issued from the digital design model is projected onto the surface of interest 20. This projection of virtual data is precise because it originates from the digital design model. This precision in the projected virtual data makes operator assembly or diagnostic operations easier to carry out. The operator is then able to detect with precision any differences between said digital design model and reality because they are highlighted by this projection.

The calibration may be optimised continuously by projecting, in addition to the digital design model and continuously, calibration patterns onto the surface of interest 20 using the video projector 19. These patterns are then captured by the image-capturing devices 18 and the transformation between said image-capturing devices 18 and the video projector 19 will then be continuously optimised, i.e. each time a new image is extracted.

Figure 2:
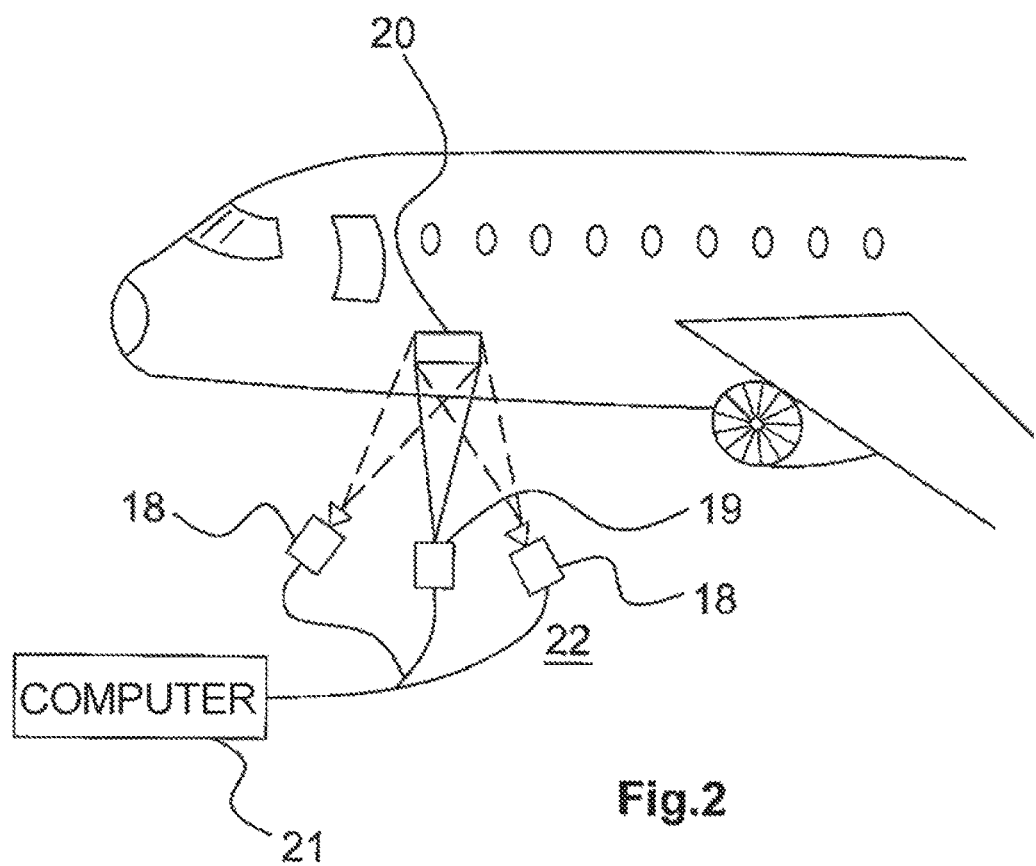
FIG. 2 illustrates a projection of virtual data according to some embodiments of the invention.

A device 22 allowing the steps of the method 10 according to one embodiment of the invention to be carried out is shown in FIG. 2. This device 22 comprises a video projector 19 and at least two image-capturing devices 18. The presence of two image-capturing devices 18 connected to a computer 21 makes it possible to obtain a three-dimensional reconstruction of the surface of interest 20, which is sensed by the image-capturing devices. The computer 21 comprises a processor and a memory and makes it possible to match characteristic points identified on the surface of interest 20 to the digital design model. The video projector 19 serves to project the virtual data directly onto the surface of interest 20 in the precise positions where an operation must be carried out.

When an image is projected with a single light source, problems are often encountered with zones of shadowing on the surface of interest 20 onto which the image is projected due to the relief of the surface of interest 20. Problems with shadowing on the surface of interest 20 may be alleviated using two to n devices 22.

The invention claimed is:

1. A method for projecting information issued from a digital design model, comprising the steps of:
calibrating by acquiring characteristic data originating from a surface of interest, comparing the characteristic data with virtual data issued from the digital design model, and determining a spatial position of a projecting device comprising a single video projector and at least two separate image-capturing devices, the calibrating step further comprises the steps of:
projecting calibration patterns onto the surface of interest;
analyzing the calibration patterns;
generating a set of correspondences between the image-capturing devices and the single video projector;
determining the spatial position of the image-capturing devices and of the single video projector based on a correspondence maximum;
identifying characteristic points on the surface of interest;
matching the characteristic points identified on the surface of interest to the digital design model; and
projecting information issued from the digital design model by the single video projector onto the surface of interest based on the spatial position.

2. The method according to claim 1, wherein the calibrating step is carried out continuously by:
projecting, in addition to the digital design model, continuously the calibration patterns and tailoring calibration to the surface of interest; and
analyzing the calibration patterns with the image-capturing devices and continuously determining the spatial position of the image-capturing devices and of the single video projector.

3. The method according to claim 1, further comprising steps of detecting and highlighting differences between the digital design model and reality.

4. The method according to claim 1, further comprising step of determining the spatial position of and tracking known movable objects in a field of view of the image-capturing devices.

5. The method according to claim 1, further comprising steps of compensating for vibrations; and generating an alarm in response to non-compensation of the vibrations.

6. The method according to claim 1, further comprising step of inhibiting shadowing on the surface of interest.

7. The method according to claim 1, further comprising step of projecting information in three dimensions.

8. A device for projecting information issued from a digital design model, comprising:
a single video projector;
at least two image-capturing devices; and
a computer, comprising a processor and a memory, configured to:
acquire characteristic data originating from a surface of interest;
compare the characteristic data with virtual data issued from the digital design model;
determine a spatial position of the image-capturing devices and of the single video projector;
identify characteristic points on the surface of interest;
match the characteristic points identified on the surface of interest to the digital design model; and the single video projector is configured to project information issued from the digital design model onto the surface of interest based on the spatial position.

9. The device according to claim 8, wherein the image-capturing devices are global-shutter video cameras.

10. The device according to claim 8, further comprising at least two sources of infrared light.

11. The device according to claim 8, further comprising an adjusting device configured to adjust settings of the image-capturing devices based on vibrations and to emit an alarm signal when the vibrations exceed threshold.

12. The device according to claim 11, wherein the adjusting device comprises an inertial sensor rigidly fastened to the single video projector.

13. The device according to claim 8, wherein the single video projector is mounted on an instrumented mechanical system comprising a position sensor.

14. The device according to claim 13, wherein the instrumented mechanical system is motorized.

15. The device according to claim 8, further comprising an autonomous power supply system.

16. The device according to claim 8, wherein all elements of the device are grouped into two housings, the first housing containing the single video projector and the image-capturing devices and the second housing containing the computer and a power supply.

* * * * *